(12) United States Patent
Grebner et al.

(10) Patent No.: US 7,500,784 B2
(45) Date of Patent: Mar. 10, 2009

(54) X-RAY DEVICE

(75) Inventors: Albert Grebner, Eckental (DE);
Herbert Kemeth, Hausen (DE);
Winfried Lurz, Fürth (DE); Manfred Schönborn, Gerhardshofen (DE)

(73) Assignee: Siemens Aktiengesellschaft, Munich (DE)

( * ) Notice: Subject to any disclaimer, the term of this patent is extended or adjusted under 35 U.S.C. 154(b) by 211 days.

(21) Appl. No.: 11/373,698

(22) Filed: Mar. 10, 2006

(65) Prior Publication Data
US 2008/0240363 A1 Oct. 2, 2008

(30) Foreign Application Priority Data
Mar. 18, 2005 (DE) .................. 10 2005 012 700

(51) Int. Cl.
*H05G 1/02* (2006.01)
*A61B 1/00* (2006.01)
(52) U.S. Cl. .................. 378/198; 378/193; 378/209
(58) Field of Classification Search .................. 378/68, 378/177, 193, 195–198, 208, 209
See application file for complete search history.

(56) References Cited

U.S. PATENT DOCUMENTS

| 6,435,715 | B1 * | 8/2002 | Betz et al. | 378/197 |
| 6,459,760 | B1 * | 10/2002 | D'Ambrosio | 378/43 |
| 6,582,120 | B2 * | 6/2003 | Schomberg | 378/197 |
| 7,254,211 | B2 * | 8/2007 | Hunt et al. | 378/20 |
| 2002/0126802 | A1 * | 9/2002 | Olson et al. | 378/208 |
| 2005/0234327 | A1 * | 10/2005 | Saracen et al. | 600/407 |

FOREIGN PATENT DOCUMENTS

| DE | 199 57 330 A1 | 7/2000 |
| DE | 19958864 A1 | 6/2001 |
| DE | 102004062473 A1 | 4/2006 |
| EP | 0 220 501 B1 | 5/1987 |

* cited by examiner

*Primary Examiner*—Irakli Kiknadze

(57) ABSTRACT

The invention relates to an X-ray device, in which an X-ray source and an X-ray detector are attached, in an opposed arrangement oriented toward a rotational axis, to a common holder capable of rotating about the rotational axis. To simplify the design of the X-ray device, it is proposed that the holder is attached to the hand of a robot displaying six axes of rotation.

15 Claims, 1 Drawing Sheet

X-RAY DEVICE

CROSS REFERENCE TO RELATED APPLICATIONS

This application claims priority to the German Application No. 10 2005 012 700.2, filed Mar. 18, 2005 which is incorporated by reference herein in its entirety.

FIELD OF INVENTION

The invention relates to an X-ray device.

BACKGROUND OF INVENTION

An X-ray device of this type is known for example from DE 199 57 330 A1. The known X-ray device is mounted on a movable trolley. It displays a C-arm fixed in a moveable manner to the trolley, to which C-arm an X-ray source and an X-ray detector are attached in an opposed arrangement. During the use of this X-ray device, in an operating theater for example, the trolley is pushed to an examination table accommodating the patient. Following the production of the X-ray exposure, the trolley is pushed away again to improve access to the patient. Pushing the disclosed X-ray device to and fro is laborious and requires a high level of effort.

SUMMARY OF INVENTION

To counteract this disadvantage and ensure the freest possible access to the patient, EP 0 220 501 B1 discloses attaching an X-ray tube to a first robot arm which is fixed to the ceiling of an examination room. An X-ray detector is attached to a second robot arm which is fixed to the floor of the examination room underneath the examination support. For the purposes of mutual adjustment of the X-ray source and the X-ray detector, a separate control unit is provided for coordinated movement of the robot arms. Practice has shown, however, that the accuracy of the movements of the robot arms is not always sufficient. This is detrimental to the quality of the X-ray exposures produced in this way. Aside from this, the second robot arm attached underneath the patient support also interferes with access to the patient.

An object of the invention is to eliminate the disadvantages inherent in the prior art. The aim is especially to specify an X-ray device which can be produced as simply and inexpensively as possible and ensures improved access to the patient. According to a further objective of the invention, the aim is to increase the degrees of freedom in the movement of the X-ray source and the X-ray detector and therefore create additional diagnostic options.

This object is achieved by the claims.

The invention provides that the holder is attached to one hand of a robot displaying six axes of rotation. It is therefore possible to traverse the holder into any desired position and furthermore move it in any presentable movement path. The holder can be completely moved away from the examination support in a simple manner, which results in considerably improved access to the patient. The fact that both the X-ray source and also the X-ray detector provided in an opposed arrangement are attached to a common holder ensures that the X-ray source and the X-ray detector are constantly in accurate alignment with each other. X-ray pictures of a high quality can be produced with the proposed X-ray device. Due to the universal movability of the robot arm, the holder can be moved in planes relative to the patient which have not been accessible for an examination with conventional C-arm X-ray appliances, for example. The proposed X-ray device is distinguished by improved diagnostic options.

A conventional robot with six axes of rotation can be used as the robot. Robots of this kind are used especially in the automobile industry and are widely present there. Robots of this kind are offered by the company KUKA at the Internet address www.kuka.com, for example.

An advantageous embodiment provides for the holder to be attached in an immovable manner with reference to the rotational axis. This simplifies production in comparison to conventional C-arm X-ray devices. All that is required is to attach a holder designed like a conventional C-arm to the hand of a conventional robot displaying six axes of rotation.

The robot can display a turntable mounted on a fixed base frame so as to be capable of rotating about a first axis of rotation. A floating link capable of swiveling about a second axis of rotation can be attached to the turntable. An arm capable of rotating about a third axis of rotation can be attached to the floating link. Furthermore, the hand can be attached to the floating link so as to be capable of rotating about a fourth axis of rotation. The hand can display a fixing element capable of rotating about the rotational axis, which for its part is capable of rotating about a fifth axis of rotation. A robot with the aforesaid features allows universal movement of the holder. When necessary, the holder can be taken far enough away from an examination support so as to ensure complete access to a patient accommodated on the examination support.

According to a further version, an electric motor capable of being controlled with a programmable controller is provided in each case for the purposes of executing a rotary movement about the axes of rotation and/or the rotational axis. This allows the storage of predefined movement sequences. The movements of the holder can be carried out quickly, precisely, and reproducibly with the proposed robot.

According to an especially advantageous embodiment, the holder is capable of rotating about the rotational axis by an angle of more than 280°, and preferably more than 300°, and particularly preferably more than 360°, by using the robot. In a complete departure from the previous design of C-arm X-ray devices, the holder is mounted on the hand of the robot so as to be capable of rotating completely. It is no longer—as in the prior art—moved along a peripheral edge of the C-arm. This significantly simplifies the design. The effort to produce the proposed X-ray device is markedly less in comparison to the conventional C-arm X-ray device. But at the same time, the degrees of freedom in the movement of the holder can be increased and therefore the diagnostic range of the X-ray device expanded.

According to a further advantageous embodiment, a program for generating a spiral movement of the holder is provided. It is therefore possible, like in an X-ray computer tomograph, to scan the patient spirally and generate a three dimensional representation of the scanned area on the basis of the results obtained in this way.

According to a further embodiment, the X-ray device includes a table, which is free of supports at least in sections, for accommodating a patient. In a divergence from the prior art, a table of this type can be executed relatively simply, e.g. rigidly. Due to the use of a robot with six axes of rotation as proposed according to the invention, the holder can be traversed quickly and simply into all positions of the section of the table that is free of supports, and moved as defined by a predefined measurement path when there.

A further embodiment provides that an apparatus is provided for controlling the rotary movement of the holder as a function of a signal measured on the patient. The signal can involve a signal corresponding to the heart beat, for example. It is therefore possible to reproduce the movement of the heart. The movements capable of being generated with the proposed robot are sufficiently quick to carry out corresponding exposures.

A further version provides that the holder displays an apparatus for setting a distance between the X-ray source and the detector. The X-ray source and the detector can therefore be brought as close as possible to the body to be examined. This allows production of especially precise X-ray exposures.

The apparatus for setting the distance can include at least one actuator apparatus capable of being electrically driven. It is therefore possible to set the distance to a predefined measure either manually or by means of a predefined program.

According to a further especially advantageous version, the holder is connected to the fixing element of the hand of the robot so as to be capable of being detached. This allows—as and when necessary—the connection and disconnection of the holder. With the holder disconnected, a patient support can be grasped and repositioned, for example, with the fixing element. The holder can then be connected again and the patient accommodated on the patient support can be examined by means of the X-ray device.

A further version provides that two of the proposed X-ray devices can be combined with each other and in fact in such a way that the holders of the two X-ray devices rotate on one and the same rotational axis. In this respect, the X-ray sources or X-ray detectors are arranged with an offset of about 90°. This especially allows complex diagnostic examinations.

BRIEF DESCRIPTION OF THE DRAWINGS

An exemplary embodiment of the invention is explained in more detail below with reference to the drawings, in which.

DETAILED DESCRIPTION OF INVENTION

Figure 1:
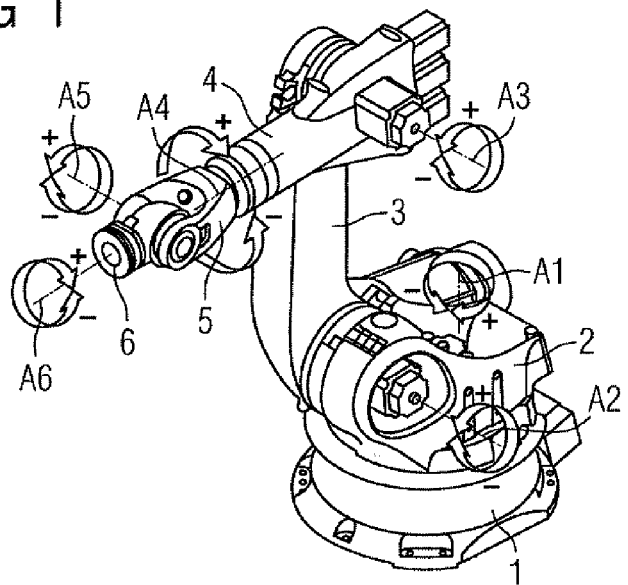
FIG. 1 shows a perspective view of a robot with six axes of rotation according to the prior art.

FIG. 1 shows a robot with six axes of rotation as disclosed according to the prior art. A turntable 2 is mounted on a base frame 1 which is installed permanently on the floor, for example, so as to be capable of rotating about a first axis of rotation A1. A floating link 3 is attached to the turntable 2 so as to be capable of swiveling about a second axis of rotation A2. An arm 4 is fixed to the floating link 3 so as to be capable of rotating about a third axis of rotation A3. A hand 5 is attached to the end of the arm 4 so as to be capable of rotating about a fourth axis of rotation A4. The hand 5 displays a fixing element 6 which is capable of rotating about a rotational axis A6 and swiveling about a fifth axis of rotation A5 running perpendicular to it.

Figure 2:
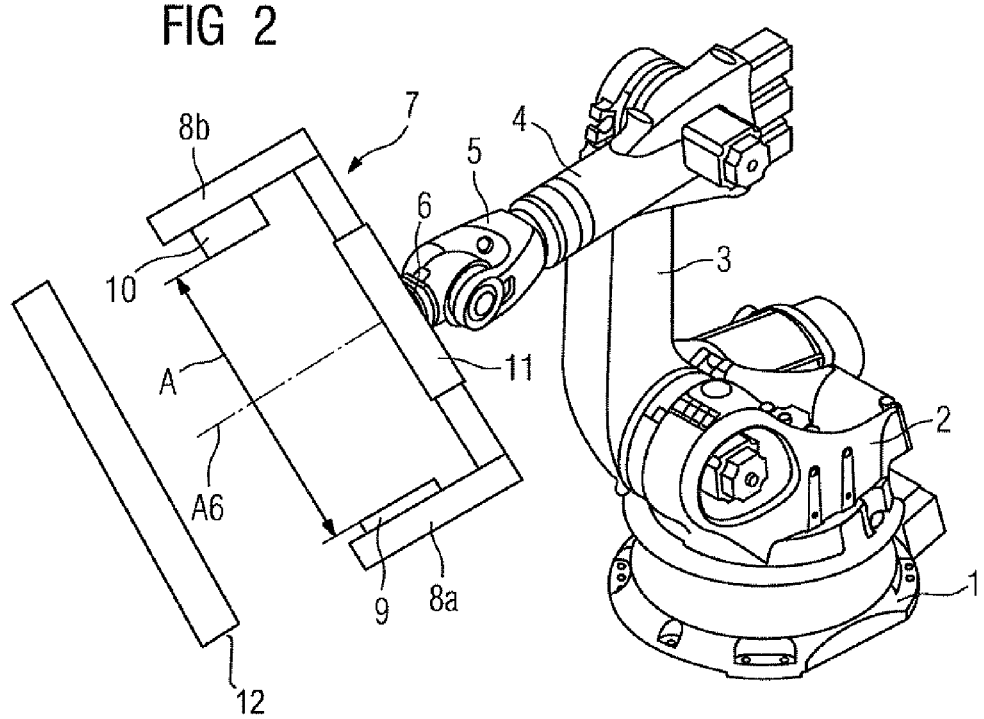
FIG. 2 shows a perspective view of an X-ray device according to the invention.

FIG. 2 shows an embodiment of the invention schematically in a perspective view. A holder generally designated by the reference symbol 7 is connected to the fixing element 6 of the hand 5. A connection not shown in detail here can be provided for this, which allows the connection and disconnection of the holder 7.

The holder 7 can be designed in the manner of a U-section with two limbs opposed to each other 8a, 8b. An X-ray detector 9 can be attached to a first limb 8a and an X-ray source 10 to a second limb 8b in an opposed arrangement. The first limb 8a and the second 8b can be attached so as to be capable of linear movement with reference to a central element 11 of the holder 7, so that a distance A between the X-ray detector 9 and the X-ray source 10 is adjustable.

The operation of the proposed X-ray device is as follows:

The base frame 1 is permanently installed on the floor or the ceiling of an examination room, for example. With the aid of the robot, the holder 7 can be traversed with reference to a patient accommodated on an examination support and brought into a predefined starting position. Then the distance A can be set to a predefined value by adjusting the two limbs 8a, 8b. For this purpose, the limbs 8a, 8b can be moved in a linear manner by means of electric motor actuators, for example.

Following this, an X-ray exposure can be produced. It is also possible to rotate the holder 7 about a predefined axis for this purpose. This can involve the rotational axis A6, for example. It is furthermore possible to rotate the holder 7 about the rotational axis A6 and traverse it axially with reference to the rotational axis A6 at the same time, for example. This results in a spiral movement which allows the reconstruction of three-dimensional pictures of structures within the body.

Finally, it is also possible to control the rotary movement of the holder 7 about the rotational axis A6 by means of signals which are generated by bodily functions measured on the patient. Thus, the movement of the holder 7 can be controlled as a function of the heart beat of the patient to be examined, for example. It is therefore possible to observe movements of the heart, and especially in a three-dimensional manner.

Control of the robot and therefore also control of the holder 7 can be effected under program control. To this extent, use can be made of conventional program control units.

Since the holder 7 is executed so as to be capable of connection to and disconnection from the fixing element 6, the robot can also be used for other purposes. Thus, for example, it is possible to connect the fixing element 6 to a patient support 12 and reposition the patient support 12, where relevant with a patient accommodated on it, with the aid of the robot. Expenditure of time and effort can therefore be avoided for medical personal.

The invention claimed is:

1. An X-ray device, comprising:
an X-ray source;
an X-ray detector, the X-ray source and the X-ray detector arranged on a common support and opposing each other, the common support rotatable about a support-related rotation axis, the X-ray source and the X-ray detector oriented towards the rotational axis; and
a robot, wherein the common support is arranged on one hand of the robot and the robot has six rotation axes including the support-related rotation axis,
wherein the robot is configured to pick up and reposition a patient support while the common support is temporarily disconnected from the robot.

2. The X-ray device according to claim 1, wherein the common support is arranged on the one hand of the robot such that the common support cannot be displaced relative to the support-related axis.

3. The X-ray device according to claim 1, wherein the robot comprises a turntable arranged on a stationary base frame, the turntable configured to be rotated about a first rotation axis included in the six rotation axes.

4. The X-ray device according to claim 3, wherein the turntable comprises a floating link configured to be swiveled about a second rotation axis included in the six rotation axes.

5. The X-ray device according to claim 4, wherein a rotational arm configured to be rotated about a third rotation axis included in the six rotation axes is arranged on the floating link.

6. The X-ray device according to claim 5, wherein the one hand is arranged on the rotational arm, the hand configured to be rotated about a fourth rotation axis included in the six rotation axes.

7. The X-ray device according to claim 1, wherein the one hand comprises a fixing element, the fixing element configured to be rotated about the support-related rotation axis and about a fifth rotation axis included in the six rotation axes.

8. The X-ray device according to claim 7, wherein the common support is detachably connected to the fixing element.

9. The X-ray device according to claim 1, further comprising an electric motor configured to be controlled by a programmable controller for executing rotary movements about the rotation axes.

10. The X-ray device according to claim 1, wherein the common support is configured to be rotated by the robot about the support-related rotation axis covering an rotation angle of at least 280°.

11. The X-ray device according to claim 1, further comprising a control program for moving the common support according to a spiral shape.

12. The X-ray device according to claim 1, wherein the patient support comprises non-supported sections.

13. The X-ray device according to claim 1, further comprising a control apparatus for rotating the common support about the support-related rotation axis based on a signal originating from a patient.

14. The X-ray device according claim 1, wherein the common support includes a device for adjusting a distance between the X-ray source and the X-ray detector.

15. The X-ray device according to claim 14, wherein the device for adjusting the distance includes at least one electrically-drivable actuator.

* * * * *